United States Patent [19]

Hill

[11] Patent Number: 5,752,961
[45] Date of Patent: May 19, 1998

[54] ANGLED SNARE ASSEMBLY

[75] Inventor: Bradley B. Hill, Lexington, Ky.

[73] Assignee: The University of Kentucky Research Foundation, Lexington, Ky.

[21] Appl. No.: 703,162

[22] Filed: Aug. 28, 1996

Related U.S. Application Data

[60] Provisional application No. 60/014,004, Mar. 25, 1996.

[51] Int. Cl.⁶ ................................. A61B 17/24
[52] U.S. Cl. .................................. 606/113; 606/110
[58] Field of Search .................. 606/37, 45, 49, 606/50, 106, 110, 113, 114, 127, 128

[56] References Cited

U.S. PATENT DOCUMENTS

| | | | |
|---|---|---|---|
| 5,059,199 | 10/1991 | Okada et al. | 606/127 |
| 5,098,440 | 3/1992 | Hillstead . | |
| 5,171,233 | 12/1992 | Amplatz et al. . | |
| 5,290,294 | 3/1994 | Cox et al. . | |
| 5,562,678 | 10/1996 | Booker | 606/108 |

FOREIGN PATENT DOCUMENTS 0027704  4/1981  European Pat. Off. ........... 606/113

OTHER PUBLICATIONS

Hubert, John W. et al.; "An Improved Snare System for Non-Surgical Retrieval of Intravascular Foreign Bodies"; 1980; Catheterization and Cardiovascular Diagnosis; vol. 6; 405–11.

*Primary Examiner*—Glenn K. Dawson
*Attorney, Agent, or Firm*—King & Schickli

[57] ABSTRACT

A snare assembly includes an outer, flexible sheath having a distal opening and a loop received for relative sliding movement with respect to the sheath. The loop has a proximal end and a distal end. The loop is formed from a resilient wire and includes a substantially 180° reverse bend at a midpoint forming the distal end and the ends of the wire are fastened together at the proximal end. A control handle is carried on the sheath for extending and retracting the loop out of and into the sheath through the distal opening. A flexible connector connects the control handle to the proximal end of the loop.

4 Claims, 3 Drawing Sheets

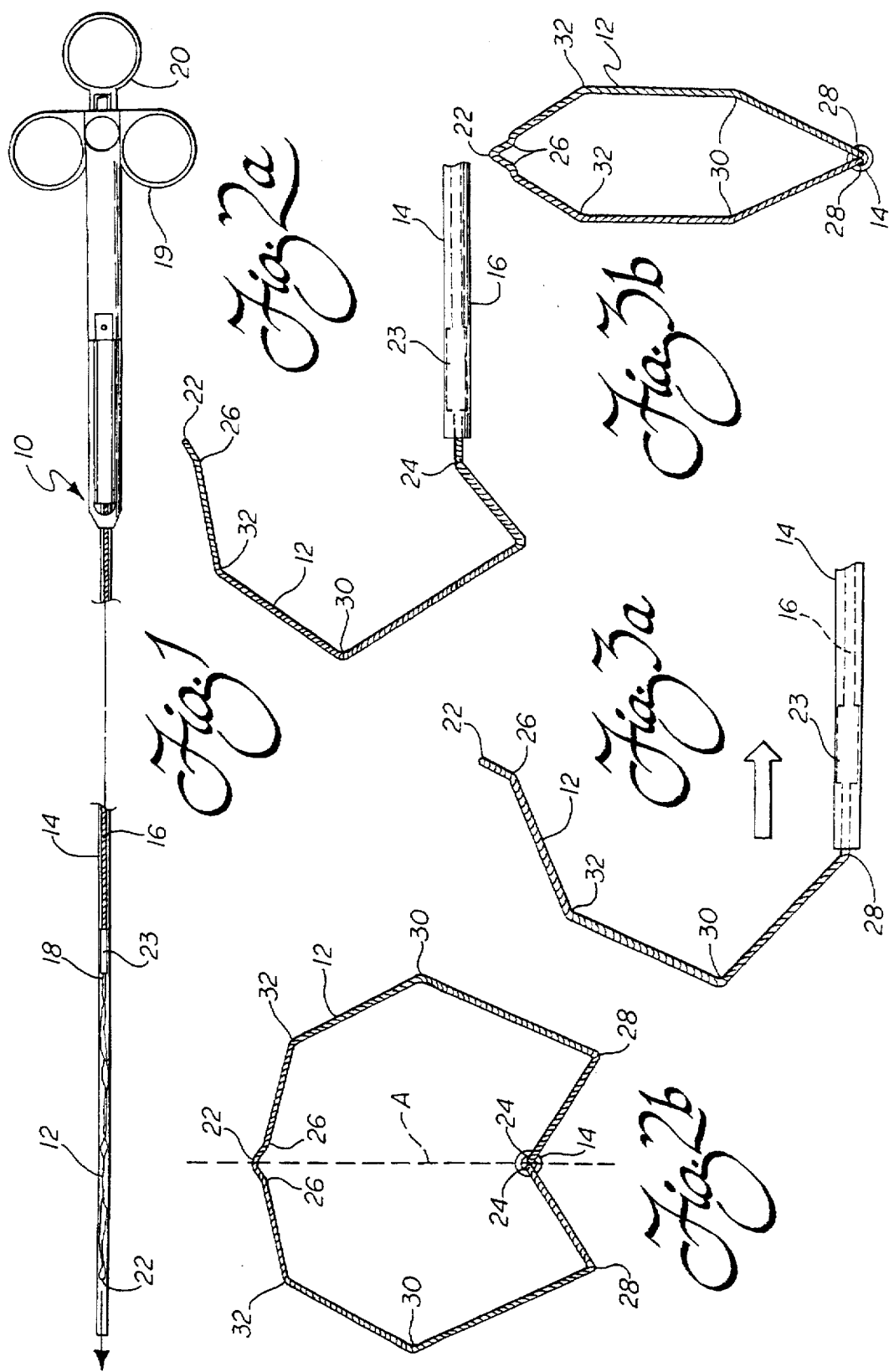

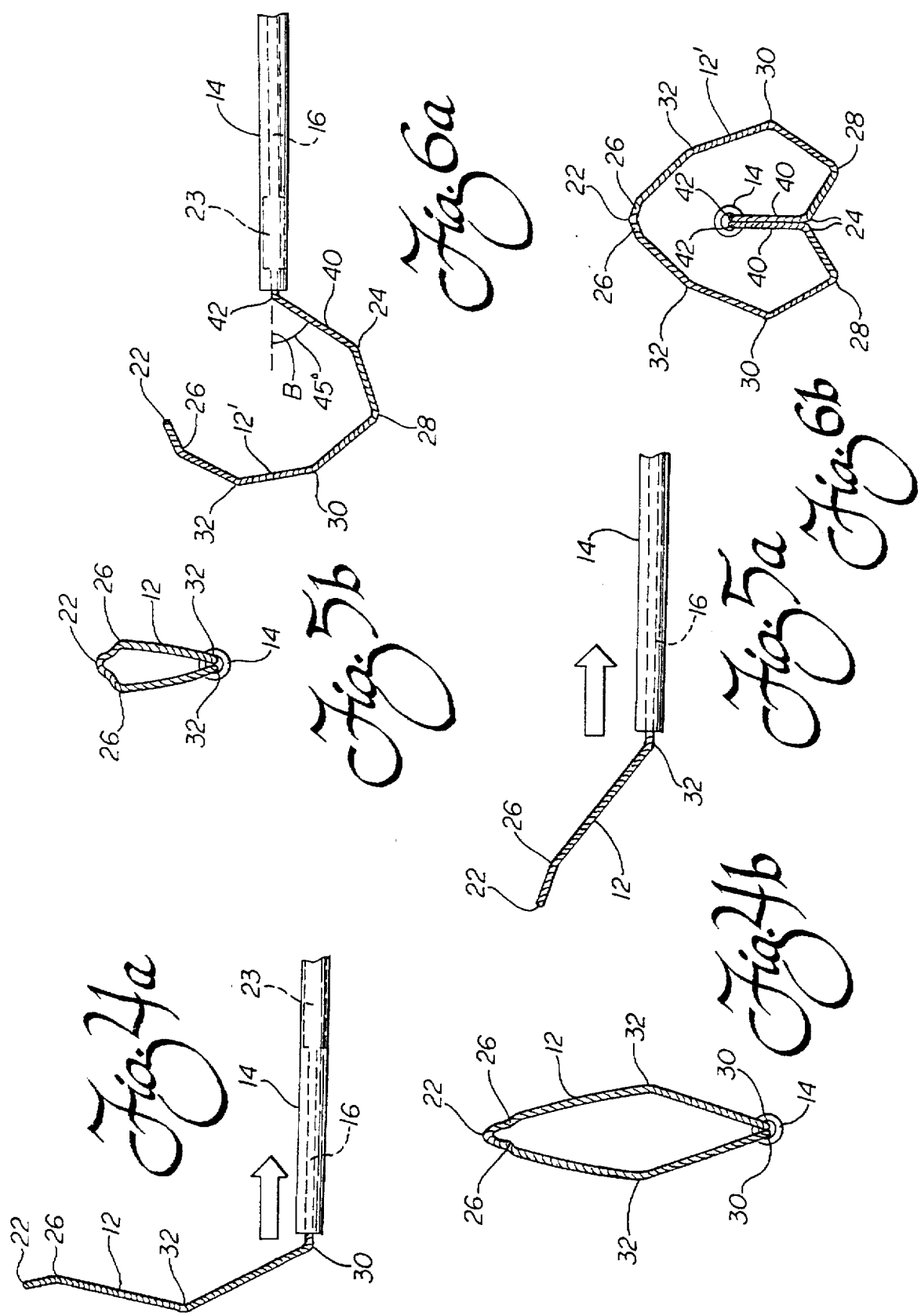

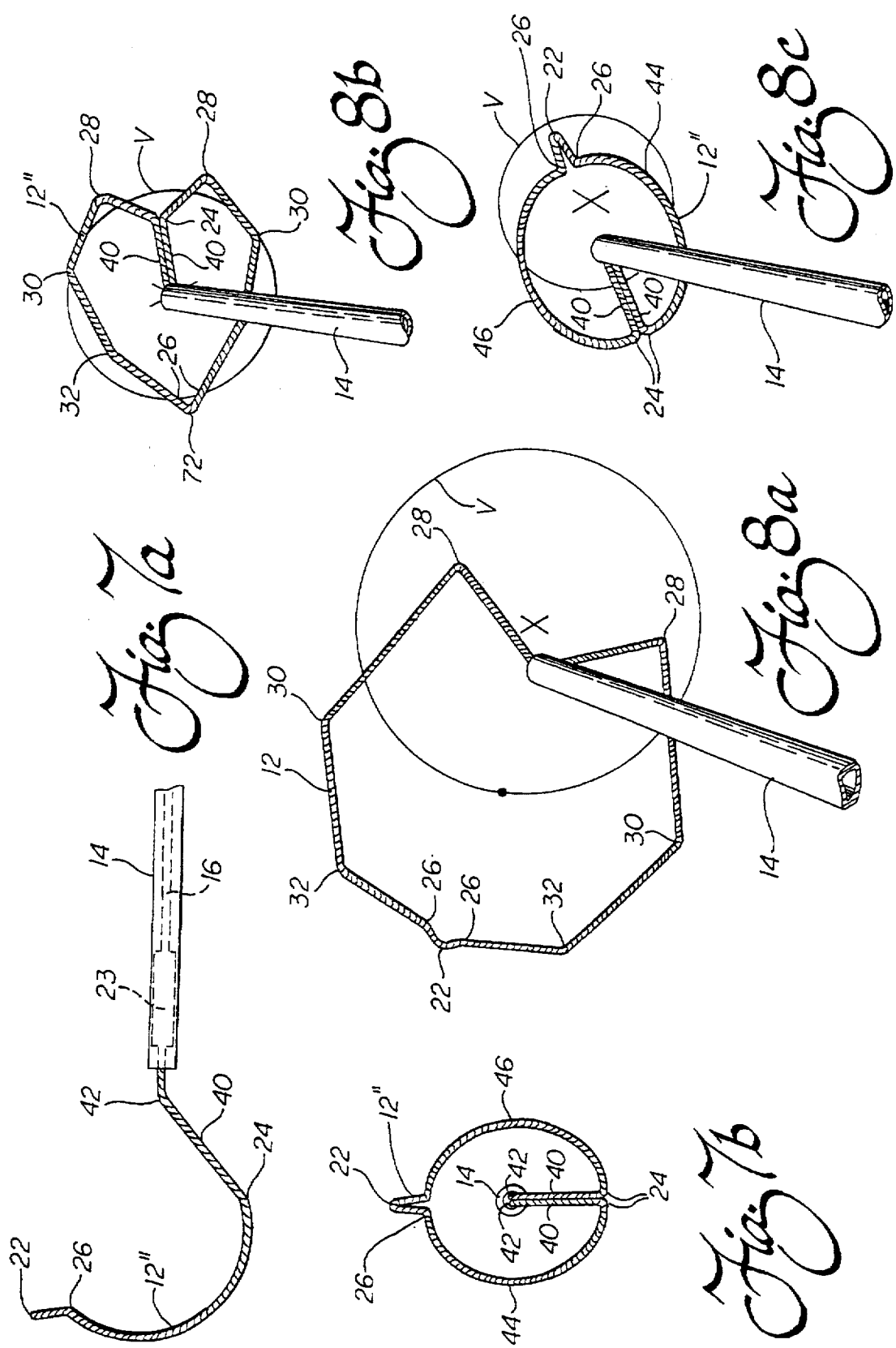

ANGLED SNARE ASSEMBLY

This application claims the benefit of U.S. provisional application Ser. No 60/014,004, filed Mar. 25, 1996.

TECHNICAL FIELD

The present invention relates generally to snare assemblies particularly useful in endoscopic, laparoscopic and like surgical procedures for grasping and retrieving tendons, other anatomical structures and foreign bodies.

BACKGROUND OF THE INVENTION

Snares, loops and lassos of various designs have long been utilized in endoscopic, laparoscopic, urethroscopic and like surgical procedures for grasping and/or retrieving tendons, other anatomical structures and even foreign bodies. The present invention relates to new and improved snare assemblies characterized by having excellent resiliency and enhanced ability to maintain an open loop substantially perpendicular to the axis of the sheath into which the loop may be retracted. This is achieved by a unique structural design that evenly distributes stress forces created when the loop is retracted into the sheath. Advantageously, the snares are much less expensive to produce than the well known Amplatz goose neck snare while providing many of the same advantages.

SUMMARY OF THE INVENTION

Accordingly, it is a primary object of the present invention to provide a snare assembly of novel design that provides reliable and dependable performance.

Another object of the present invention is to provide a snare assembly including an outer sheath, a loop, a control handle for manipulating the loop and a connector for connecting the control handle to the loop. Advantageously, the angled loop has symmetrical bends that evenly distribute stress and minimize deformation during repeated expansions from and retractions into the sheath. Accordingly, the loop is not flattened by the stress forces and accordingly, the loop retains resiliency while maintaining the ability to fully open when extended from the sheath so as to allow the grasping and retrieval of foreign bodies, tendons or other desired anatomical structures.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, an improved angled snare assembly is provided. The angled snare assembly includes a flexible outer sheath, a loop formed from resilient wire having a proximal end and a distal end, a control handle for manipulating the loop and a connector for connecting the control handle to the proximal end of the loop. The resilient wire forming the loop includes a substantially 180° reverse bend at the midpoint and a pair of ends that are fastened together. The 180° reverse bend forms an apex at the distal end of the loop and the fastened together ends form the proximal end connected to the connector.

Still further describing the invention, the loop includes a pair of sections, one section being defined between each end and the apex. The sections also include matching symmetrical bends at spaced locations. More particularly, a first pair of matching symmetrical bends are located adjacent the fastened ends and a second pair of mirror image symmetrical bends are located adjacent the apex while leaving the 180° bend of the apex unaltered. Further, three additional matching symmetrical bends are located on the sections so as to divide the sections between the first and second symmetrical bends into four segments of substantially equal length. Each of the first, second and three additional bends are made at an angle of substantially 45° away from the loop axis defined as an imaginary line bisecting the apex and the fastened ends of the wire strip.

In accordance with yet another aspect of the present invention the resilient wire may assume the form of a wire strip. The first, second and three additional symmetrical bends are made in alternating first and second (i.e. downward and upward, directions. Thus, the first bend is made in a first direction (downward), the next adjacent additional bend is made in a second, opposite direction (upward), the next adjacent additional bend is made in the first direction downward, the next adjacent additional bend is made in the second direction upward and the second bend is made in the first direction (downward).

Advantageously, this "alternating direction" bend arrangement with all sectional bends of less than or equal to 45° insures that the loop maintains resiliency even following multiple retractions inside the sheath. The bends effectively distribute the stress in a manner that minimizes deformation during repeated expansions from and retractions within the sheath. Thus, the snare always opens widely with excellent resiliency. Further, three different sizes of loops are spontaneously formed as the snare is pushed out of or withdrawn into the sheath as a result of the unique interloop bends.

In accordance with still another aspect of the present invention, the loop may include a depending segment between the first pair of matching symmetrical bends and the connector. More specifically, the depending segment includes a pair of matching offset bends defining an angle of substantially 30°–70° and, more preferably approximately 45° from a longitudinal axis defined by a distal end of the sheath. This structural arrangement effectively aligns the center of the fully extended loop with the viewing field of the scope with which this snare assembly is being utilized. This allows more convenient and accurate line of sight manipulation of the snare assembly. This is very important when utilizing the loop to grasp and retrieve tendons, other anatomical structures such as polyps and foreign bodies.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawing incorporated in and forming a part of the specification, illustrates several aspects of the present invention and together with the description serves to explain the principles of the invention. In the drawing:

FIG. 1 is a side elevational view of the angled snare assembly of the present invention wherein the angled snare is fully withdrawn into its sheath;

FIG. 2a is a detailed side elevational view of the angled snare assembly shown in FIG. 1 but with the angled snare fully extended from its sheath;

FIG. 2b is an end elevational view showing the extended angled snare of FIG. 2a;

FIGS. 3a and 3b are, respectively, detailed side and end elevational views showing the snare assembly of FIGS. 2a and 2b in a first intermediate position;

FIGS. 4a and 4b are, respectively, detailed side and end elevational views showing the snare assembly of FIGS. 2a and 2b in a second intermediate position;

FIGS. 5a and 5b are, respectively, detailed side and end elevational views showing the snare assembly of FIGS. 2a and 2b in a third intermediate position;

FIGS. 6a and 6b are, respectively, detailed side and end elevational views of an alternative concentric angled snare in a fully extended position;

FIGS. 7a and 7b are, respectively, detailed side and end elevational views of an additional alternative concentric curved snare in a fully extended position; and FIGS. 8a–c are schematical perspective views illustrating the viewing field relative to the three snare embodiments of the present invention when in the fully extended position with FIG. 8a showing the angled snare of FIGS. 2a and 2b, FIG. 8b showing the concentric curved snare of FIGS. 6a and 6b and FIG. 8c showing the concentric curved snare of FIGS. 7a and 7b.

Reference will now be made in detail to the present preferred embodiment of the invention, an example of which is illustrated in the accompanying drawing.

DETAILED DESCRIPTION OF THE INVENTION

The snare assembly 10 is a grasping and retrieving device that can be introduced into an anatomic space through a remote access site via an endoscope working channel or a port as in laparoscopic surgery. The snare assembly 10 shown in FIGS. 1, 2a, 2b, 3a, 4a, 4b, 5a, 5b and 7a consists of an angled loop 12, a flexible and tubular sheath 14, a flexible coaxial wire connector 16 that is attached to a proximal end 18 of the loop, and a handle 20 of a type known in the art including a relatively sliding actuator 19 that is used to expand and retract the angled loop. The angled loop 12 can be made of a variety of materials—stainless steel, hydrocarbon polymer, nitinol, or other round wire braided wire or wire strip. The material that constitutes the loop 12 must have adequate pliability and resiliency so that it can maintain its shape satisfactorily with multiple expansions and retractions into the sheath 14.

The sheath 14 should be made of a flexible but strong hydrocarbon polymer that resists crimping and compression along its longitudinal axis. The coaxial wire connector 16 resides inside the sheath 14 and is attached to the folded loop 12 at one end by a clip 23 of a type known in the art and the sliding actuator 19 of the operator handle 20 on the other end by a fastener 25. The wire connector 16 should be made of a strong and flexible material that resists crimping. The loop 12 has symmetrical bends that evenly distribute stress and minimize deformation during repeated expansions and retractions within the sheath 14.

A loop 12 is made by bending a round wire, braided wire, thin strip of flat wire or other pliable material 180°, at its midpoint, so that its two ends are pressed against one another. For descriptive purposes, the two half sections created by this bending will be termed "hemiloops". A line drawn along the length of the two hemiloops, in between them will be termed the "axis" A (see FIG. 2b), and the reverse bend 22 at the distal end of the loop will be termed the "apex". The free ends are fastened together by soldering or other means. If the loop 12 is opened and looked down upon from above such that the fastened ends of the loop are on the right side and the apex is on the left side, the first pair of angled bends 24 is made in a symmetrical fashion adjacent to the fastened ends on the right side of the loop. This is accomplished by bending the left side of each hemiloop (in a first direction) downward and outward away from the loop axis at a substantially 45° angle.

Next mirror image angled bends 26, downward and outward away from the loop axis at substantially a 45° angle, are made on the left side of the loop a short distance from the apex 22. This "short distance" from the apex 22 should be just long enough so that the 180° apex bend 22 is not altered by the angled bends 26 on each side. The distance between the two pairs of angled bends 24, 26 on the right and left sides of the loop 12, is termed the "interloop distance".

The interloop distance is divided into four segments of approximately equal length. The four segments of each hemiloop are separated by three "interloop" angled bends 28, 30, 32. All interloop bends 28, 30, 32 are made in reference to the loop axis A with the loop in its original flat or straightened position along the axis. The first pair of interloop bends 28 are made at one fourth the interloop distance from the pair of angled bends 24 on the right hand side of the loop. This is accomplished by bending the left hand side of each hemiloop (in a second direction) upward and outward at a 45° angle from the loop axis A. The second pair of interloop bends 30 are made at one half the interloop distance from the pair of angled bends 24 on the right hand side of the loop 12. This is done by bending the left side of each hemiloop downward and outward at a 45° angle from the loop axis A. The third pair of interloop bends 32 are made at three fourths the interloop distance from the pair of angled bends 24 on the right side of the loop 12. This is done by bending the left hand side of each hemiloop upward and outward at a 45° angle from the loop axis A. The angular orientation of the bends is best understood with reference to FIGS. 2a and 2b.

The loop 12 is retracted inside its sheath 14 by manipulating the sliding actuator 19 so as to pull the proximal end of the loop, the original free ends, into the sheath (see FIG. 1). The loop 12 is expanded by sliding the actuator 19 so as to push the loop out of the sheath 14. When constructed properly and with appropriate materials, the snare opens widely and has excellent resiliency. An advantage of this specific design is the fact that four sizes of loops 12 form as the loop is pushed out of the sheath 14 because of the positions of the unique interloop bends 24, 26, 28, 30, 32 (see FIGS. 3a–3b showing the first intermediate position, FIGS. 4a and 4b showing the second intermediate position, FIGS. 5a and 5b showing the third intermediate position and, of course, FIGS. 2a and 2b showing the fully open position). It should be noted that each size loop projects at an angle from the plane in which the sheath 14 extends longitudinally (note particularly, FIGS. 2a, 2b, 3a, 3b, 4a, 4b, 5a and 5b). This allows an improved viewing field when manipulating the snare assembly 10 to grasp objects. Also allows the grasping of different size objects: that is, the assembly 10 provides loops of four different sizes to meet the needs of the surgeon without the necessity of changing snare assemblies. This is a versatility heretofore unseen in the art.

A first alternative embodiment of the present invention is shown in FIGS. 6a and 6b. Specifically, a concentric angle snare loop 12' is shown in a fully extended position. For purposes of simplicity of illustration and description, the bends of the snare assembly 10 shown in FIGS. 1, 2a, 2b, 3a, 3b, 4a, 4b, 5a and 5b are identified by the same reference numerals in FIGS. 6a and 6b showing the concentric angled snare 10'. It should be appreciated, however, that concentric angled snare loop 12' includes an additional depending segment 40 between the first pair of matching symmetrical bends 24 and the clip 19 of the connector 20. More specifically, the depending segment includes a pair of matching offset bends 42 that define an angle of substantially 30°–70° and more preferably approximately 45° from a longitudinal axis B defined by the distal end of the sheath 14 as best shown in FIG. 6a.

As a result, it should be appreciated, that the first pair of matching symmetrical bends 24 in the concentric angled snare loop 12' shown in FIGS. 6a and 6b are offset from the longitudinal axis the and not aligned with the longitudinal axis A as in the first embodiment of the invention shown in FIG. 2a. This is an important modification when one considers the fact that the snare assembly 10 is to be manipulated through the working channel or port of an endoscope. Specifically, as shown in FIG. 8a, in the first, angled snare loop 12 embodiment, a large portion of the loop extends outside the visual field V provided through the endoscope. In contrast, the depending segment 30 of the concentric angled snare loop 12' offsets the first pair of matching symmetrical bends 24 so that the concentric angled snare loop is substantially centered with respect to the viewing field V (note particularly, FIG. 8b). The fact that the loop 12' is substantially centered upon the viewing field V may be particularly helpful as a surgeon manipulates the snare assembly to grasp and retrieve tendons as well as other anatomical structures and even foreign bodies.

Still another embodiment is shown in FIGS. 7a, 7b and 8c. Specifically, these figures show a concentric curved snare loop 12". As shown, this snare loop 12" incorporates the offset segment 40, the first pair of matching symmetrical bends 24, the second pair of matching symmetrical bends 26 and the substantially 180° bend 22 at the midpoint. There are, however, no interloop angles dividing the pair of opposing sections or hemiloops into segments. Accordingly, the sections/hemiloops 44, 46 defined between the first and second pair of matching symmetrical bends 24, 26 are formed as smooth curves. The relationship of the loop 12" relative to the viewing field V of an endoscope in which the device is utilized is shown in FIG. 8c.

In summary, numerous benefits result from employing the concepts of the present invention. The snare assembly 10 includes a loop 12 that is formed from symmetrical hemiloop bends of less than or equal to 45° that evenly distribute stress and minimize deformation during repeated expansions from and retractions into the sheath. Accordingly, the loop is not flattened by stress forces and retains resiliency and its desired shape so that it will fully open when extended from the sheath in order to allow grasping and retrieval of foreign bodies, tendons and other desired anatomical structures.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

I claim:

1. A snare assembly comprising:

an outer sheath having a distal opening and a longitudinal axis extending in a first plane;

a loop having a proximal end and a distal end, said loop being formed from a resilient wire that includes a reverse bend at a midpoint and a pair of ends fastened together, said reverse bend forming an apex at said distal end of said loop and said fastened together ends forming said proximal end;

a control handle for extending and retracting said loop out of and into said sheath through said distal opening, said loop projecting at an angle from said first plane into a second plane when extended from said distal opening; and a connector for connecting said control handle to said proximal end of said loop; and said snare assembly being further characterized by said loop including a pair of hemiloops, one hemiloop being defined between each of said pair of ends and said apex, said hemiloops including matching symmetrical bends at spaced locations;

a first pair of said matching symmetrical bends being located adjacent said fastened together ends and a second pair of mirror image matching symmetrical bends being located adjacent said apex; and three additional matching symmetrical bends being located on each of said hemiloops so as to divide said hemiloops between said first and second pair of matching symmetrical bends into four segments of substantially equal length.

2. The snare assembly set forth in claim 1, wherein each of said three additional matching additional symmetrical bends are made to define and included angle less than or equal to 45°.

3. The snare assembly set forth in claim 1, wherein said first pair of matching symmetrical bends are substantially aligned with said distal opening along the longitudinal axis.

4. The snare assembly set forth in claim 1, wherein said loop includes a depending segment between said first pair of matching symmetrical bends and said connector, said depending segment including a pair of matching offset bends defining an angle of substantially 30°–70° from the longitudinal axis.

* * * * *